United States Patent
Carpenter et al.

(10) Patent No.: US 9,498,513 B2
(45) Date of Patent: Nov. 22, 2016

(54) ANTIMICROBIAL BACTERIA STRAINS AND USES THEREOF

(71) Applicant: Fraunhofer USA Inc., Newark, DE (US)

(72) Inventors: Megan R. Carpenter, Wilmington, DE (US); Zusheng Li, Newark, DE (US); Vadim Mett, Newark, DE (US); Vidadi Yusibov, Havertown, PA (US)

(73) Assignee: Fraunhofer USA Inc., Newark, DE (US)

( * ) Notice: Subject to any disclaimer, the term of this patent is extended or adjusted under 35 U.S.C. 154(b) by 0 days.

(21) Appl. No.: 14/843,218

(22) Filed: Sep. 2, 2015

(65) Prior Publication Data

US 2015/0359844 A1 Dec. 17, 2015

Related U.S. Application Data

(62) Division of application No. 13/643,143, filed as application No. PCT/US2011/033892 on Apr. 26, 2011, now Pat. No. 9,156,893.

(60) Provisional application No. 61/327,939, filed on Apr. 26, 2010.

(51) Int. Cl.
| | |
|---|---|
| *A61K 38/16* | (2006.01) |
| *A01N 63/00* | (2006.01) |
| *A01N 63/02* | (2006.01) |
| *C07K 14/195* | (2006.01) |
| *C12R 1/01* | (2006.01) |
| *C12R 1/46* | (2006.01) |
| *C12N 1/20* | (2006.01) |
| *A61K 35/00* | (2006.01) |

(52) U.S. Cl.
CPC ............. *A61K 38/164* (2013.01); *A01N 63/00* (2013.01); *A01N 63/02* (2013.01); *C07K 14/195* (2013.01); *C12N 1/20* (2013.01); *C12R 1/01* (2013.01); *C12R 1/46* (2013.01); *A61K 2035/115* (2013.01)

(58) Field of Classification Search
CPC .................................................. A01N 63/00
See application file for complete search history.

(56) References Cited

U.S. PATENT DOCUMENTS 7,494,810 B2    2/2009  Kuhner et al.

FOREIGN PATENT DOCUMENTS

| WO | WO 00/12528 | 3/2000 |
| WO | WO 03/066880 A2 | 8/2003 |

OTHER PUBLICATIONS

Database Geneseq [Online] XP-002655641, Accession No. EU723825 (2008).
Anandaraj et al., Biochemical and Biophysical Research Communications, 379:179-85 (2009).
Casaus et al., Microbiology, 143:2287-94 (1997).
Chernin et al., Current Microbiology, 32:208-12 (1996).
Chung et al., Int'l J. Systematic and Evolutionary Microbiology, 50:1495-1500 (2000).
He et al., Applied and Environmental Microbiology, 73(1):168-78 (2007).
Henriksen et al., Letters in Applied Microbiology, 45:491-96 (2007).
R.D. Joerger, Poultry Science, 82(4):640-47 (2003).
Kalbe et al., Microbiological Research, 151(4);433-39 (1996).
Kang and Lee, J. Applied Microbiology, 98:1169-76 (2005).
Kwaadsteniet et al., Int'l Journal of Food Microbiology, 105:433-44 (2005).
Martin et al., J. Biological Chemistry, 278(15):13124-132 (2003).
Piuri et al., Letters in Applied Microbiology, 27:9-13 (1998).
Raaijmakers et al., Antonie van Leeuwenhoek, 81:537-47 (2002).
Sabia et al., Letters in Applied Microbiology, 38:99-105 (2004).
Selim et al., Applied and Environmental Microbiology, 71(11):6501-07 (2005).
Thomson et al., Molecular Microbiology, 36(3):539-56 (2000).
Tupinamba et al., Journal of Applied Microbiology, 105:1044-53 (2008).
Vuyst and Frédéric, J. Molecular Microbiology and Biotechnology, 13(4):194-99 (2007).
Wright et al., Applied and Environmental Microbiology, 67(1):284-92 (2001).
Zhang et al., Antimicrobial Agents and Chemotherapy, 49(7):2921-27 (2005).
PCT/US2011/033892 International Search Report by European Patent Office mailed Sep. 14, 2011.

*Primary Examiner* — Bin Shen
(74) *Attorney, Agent, or Firm* — RatnerPrestia

(57) ABSTRACT

The present invention provides novel antimicrobial bacteria strains and uses thereof to prepare novel antimicrobial agents. Also provided are the novel antimicrobial agents.

4 Claims, 4 Drawing Sheets

Figure 1

| | |
|---|---|
| tggagagttt gatcctggct caggacgaac gctggcggcg tgcctaatac atgcaagtcg | 60 |
| agcggagaat raargaagct tgcttctttc attcttagcg gcggacgggt gagtaacacg | 120 |
| taggcaacct gccctcaagc ttgggacaac taccggaaac ggtagctaat accgaataca | 180 |
| tgatttgttc gcctgaacga atytggaaag acggagcaat ctgtcacttg aggatgggcc | 240 |
| tgcggcgcat tagctagttg gtgaggtaac ggctcaccaa ggcgacgatg cgtagccgac | 300 |
| ctgagagggt gatcggccac actgggactg agacacggcc cagactccta cgggaggcag | 360 |
| cagtagggaa tcttccgcaa tggacgcaag tctgacggag caacgccgcg tgagtgatga | 420 |
| aggttttcgg atcgtaaagc tctgttgcca gggaagaacg tcygrgttag taactgaact | 480 |
| crgagtgacg gtacctgaga agaaagcccc ggctaactac gtgccagcag ccgcggtaat | 540 |
| acgtaggggg caagcgttgt ccggaattat tgggcgtaaa gcgcgcgcag gcggcttttt | 600 |
| aagtccggtg tcacagccca aggctcaacc ttgggtcgca ctggaaactg gagagcttga | 660 |
| gtacagaaga ggaaagtgga attccacgtg tagcggtgaa atgcgtagag atgtggagga | 720 |
| acaccagtgg cgaaggcgac tttctgggct gtaactgacg ctgaggcgcg aaagcgtggg | 780 |
| gagcaaacag gattagatac cctggtagtc cacgccgtaa acgatgaatg ctaggtgtta | 840 |
| ggggtttcga taccttggt gccgaagtta acacattaag cattccgcct ggggagtacg | 900 |
| gtcgcaagac tgaaactcaa aggaattgac ggggacccgc acaagcagtg gagtatgtgg | 960 |
| tttaattcga agcaacgcga agaaccttac caagtcttga catccctttg accggactag | 1020 |
| agatagtcct ttccttcggg acaaaggaga caggtggtgc atggttgtcg tcagctcgtg | 1080 |
| tcgtgagatg ttgggttaag tcccgcaacg agcgcaaccc ttatgcttag ttgccagcac | 1140 |
| atcatggtgg gcactctaag cagactgccg gtgacaaacc ggaggaaggt ggggatgacg | 1200 |
| tcaaatcatc atgccccta tgacttgggc tacacacgta ctacaatggc cggtacaacg | 1260 |
| ggaagcaata tcgcaagatg gagccaatcc ttaaaagccg gtctcagttc ggattgcagg | 1320 |
| ctgcaactcg cctgcatgaa gtcggaattg ctagtaatcg cggatcagca tgccgcggtg | 1380 |
| aatacgttcc cgggtcttgt acacaccgcc cgtcacacca cgagagtttg caacacccga | 1440 |
| agtcggtggg gtaaccgcaa ggagccagcc gccgaaggtg gggtagatga ttggggtgaa | 1500 |
| gtcgtaacaa ggtagccgta tcggaaggtg cggytggatc acctcctt | 1548 |

Figure 2

| | |
|---|---|
| tggagagttt gatcctggct caggacgaac gctggcggcg tgcctaatac atgcaagtcg | 60 |
| aacgctttt cttcaccgg agcttgctcc aycgaaagaa aaagagtggc gaacgggtga | 120 |
| gtaacacgtg ggtaacctgc ccatcagaag gggataacac ttggaaacag gtgctaatac | 180 |
| cgtataacac tattttccgc atggaagaaa gttgaaaggc gcttttgcgt cactgatgga | 240 |
| tggacccgcg gtgcattagc tagttggtga ggtaacggct caccaaggca acgatgcata | 300 |
| gccgacctga gagggtgatc ggccacactg ggactgagac acggcccaga ctcctacggg | 360 |
| aggcagcagt agggaatctt cggcaatgga cgaaagtctg accgagcaac gccgcgtgag | 420 |
| tgaagaaggt tttcggatcg taaaactctg ttgttagaga agaacaagga tgagagtaaa | 480 |
| acgttcatcc cttgacggta tctaaccaga aagccacggc taactacgtg ccagcagccg | 540 |
| cggtaatacg taggtggcaa gcgttgtccg gatttattgg gcgtaaagcg agcgcaggcg | 600 |
| gtttcttaag tctgatgtga agccccgg ctcaaccggg gagggtcatt ggaaactggg | 660 |
| agacttgagt gcagaagagg agagtggaat tccatgtgta gcggtgaaat gcgtagatat | 720 |
| atggaggaac accagtggcg aaggcggctc tctggtctgt aactgacgct gaggctcgaa | 780 |
| agcgtgggga gcgaacagga ttagataccc tggtagtcca cgccgtaaac gatgagtgct | 840 |
| aagtgttgga gggtttccgc ccttcagtgc tgcagcaaac gcattaagca ctccgcctgg | 900 |
| ggagtacgac cgcaaggttg aaactcaaag gaattgacgg gggcccgcac aagcggtgga | 960 |
| gcatgtggtt taattcgaag caacgcgaag aaccttacca ggtcttgaca tcctttgacc | 1020 |
| actctagaga tagagcttcc ccttcggggg caaagtgaca ggtggtgcat ggttgtcgtc | 1080 |
| agctcgtgtc gtgagatgtt gggttaagtc ccgcaacgag cgcaacccct attgttagtt | 1140 |
| gccatcattt agttgggcac tctagcgaga ctgccggtga caaaccggag gaaggtgggg | 1200 |
| atgacgtcaa atcatcatgc cccttatgac ctgggctaca cacgtgctac aatgggaagt | 1260 |
| acaacgagtt gcgaagtcgc gaggctaagc taatctctta aagcttctct cagttcggat | 1320 |
| tgtaggctgc aactcgccta catgaagccg gaatcgctag taatcgcgga tcagcacgcc | 1380 |
| gcggtgaata cgttcccggg ccttgtacac accgcccgtc acaccacgag agtttgtaac | 1440 |
| acccgaagtc ggtgaggtaa cctttttgga gccagccgcc taaggtggga tagatgattg | 1500 |
| gggtgaagtc gtaacaaggt agccgtatcg gaaggtgcgg ctggatcacc tcctt | 1555 |

ANTIMICROBIAL BACTERIA STRAINS AND USES THEREOF

CROSS REFERENCE TO RELATED APPLICATIONS

This patent application is a divisional application of U.S. application Ser. No. 13/643,143, filed Feb. 7, 2013, now U.S. Pat. No. 9,156,893, which is a U.S. national stage Application of International Application No. PCT/US2011/033892, filed Apr. 26, 2011, claiming priority to U.S. Provisional Application No. 61/327,939, filed Apr. 26, 2010, the contents of each of which are incorporated by reference in their entireties for all purposes.

FIELD OF THE INVENTION

This invention relates to identification of novel antimicrobial bacteria strains and use of these antimicrobial bacteria strains to prepare novel antimicrobial agents.

BACKGROUND OF THE INVENTION

Over the last few years, antibiotic-resistant bacteria have been isolated in increasing numbers, but anti-microbial drugs are losing their effectiveness. For some infections, such as those caused by methicillin resistant *S. aureus* (MRSA) and multi-drug resistant (MDR) *A. baumannii*, there are virtually no antibiotics available for treatment. For many other infections, the choice of antibiotics is rapidly diminishing.

Based on PCR technology and comparative microbial genome sequencing, it has been estimated that only 1-5% of existing bacteria have been cultured in the laboratory. The ability to cultivate new species in the laboratory offers the ability to isolate novel compounds useful in many industries.

Novel bacteria exhibiting antimicrobial properties are useful in light of the increasing number of infections due to antimicrobial resistance. Because many microbes are resilient and develop resistance, there is a pressing need for the development of new anti-microbial agents by identifying and isolating novel bacteria with antimicrobial properties.

SUMMARY OF THE INVENTION

The present invention relates to novel antimicrobial microorganisms and their uses to prepare novel antimicrobial agents.

An isolated microorganism of the genus *Paenibacillus* is provided as deposited with the American Type Culture Collection (ATCC®) on Apr. 26, 2011, having an ATCC®Patent Deposit Designation of PTA-11858. A functionally equivalent microorganism of the isolated microorganism is also provided. The functionally equivalent microorganism may comprise a 16S rRNA sequence at least 95% identical to SEQ ID NO:1. A biological culture of the microorganism of the present invention, or a functionally equivalent microorganism thereof, is further provided.

In some embodiments, an antimicrobial agent is prepared by using the microorganism of the present invention, or a functionally equivalent microorganism thereof. The antimicrobial agent may be prepared from a biological culture of the microorganism, or a functionally equivalent microorganism thereof. The antimicrobial agent may also be prepared from a supernatant of a biological culture of the microorganism, or a functionally equivalent microorganism thereof.

The antimicrobial agent may comprise an amino acid sequence selected from the group consisting of SEQ ID NOs: 3-18. Also provided is a method for preparing an antimicrobial agent. The method comprises using the microorganism of the present invention, or a functionally equivalent microorganism thereof.

In some other embodiments, a method for treating a microbial infection in a subject in need thereof is provided. The method comprises administering to the subject an effective amount of an antimicrobial agent. The antimicrobial agent is prepared by using the microorganism of the present invention, or a functionally equivalent microorganism thereof.

BRIEF DESCRIPTION OF THE DRAWINGS

FIG. 1 illustrates the 16S rRNA sequence (SEQ ID NO: 1) of Isolate G346a (ATCC accession number PTA-11858).

FIG. 2 illustrates the 16S rRNA sequence (SEQ ID NO: 2) of Isolate 159.

DETAILED DESCRIPTION OF THE INVENTION

Figure 3:
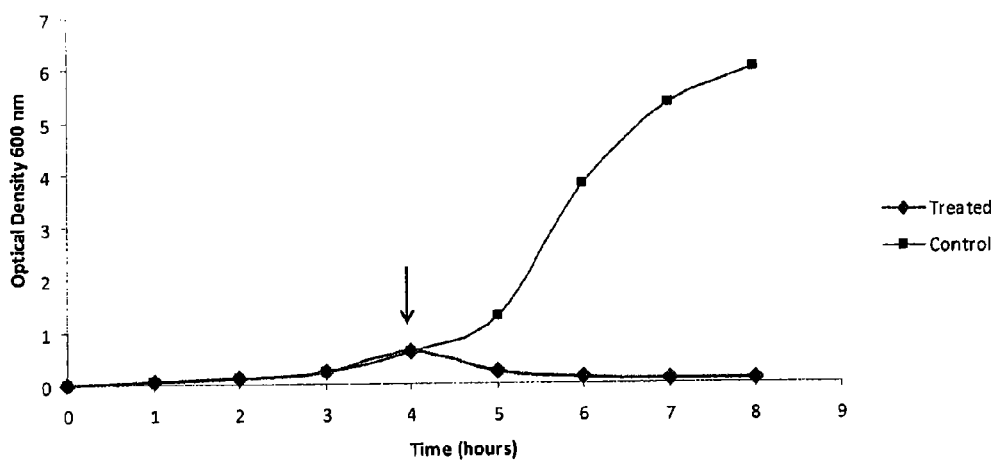
FIG. 3 illustrates the antimicrobial activity of Isolate G346a (ATCC accession number PTA-11858) against *Staphylococcus aureus* (*S. aureus*).

While 70 out of 90 antibiotics marketed between 1982-2002 originated from natural sources, the majority (98%) of microorganisms believed to exist have never been cultured. Thus, these previously uncultured microbes offer tremendous potential for new antibiotics. The present invention is based on the discovery of new, previously uncultured microorganisms with antimicrobial activity and the use of these microorganisms to prepare new antimicrobial agents or antibiotics.

According to one aspect of the present invention, microorganisms having an antimicrobial activity are provided. Examples of these antimicrobial microorganisms include bacterial strains identified as novel Isolates Nos. 6, 17, 138, 159, 228, 375, 423, 457, G266, G280, G346a, G505, G507, G522, and G524.

The term "antimicrobial activity" used herein refers to an activity to prevent or inhibit (or reduce) the growth of, or to kill certain microorganisms, including Gram-positive and/or Gram negative bacteria strains, especially those related to currently known antibiotic resistant strains.

Bacterial strains against which these novel isolates have been tested include *Staphylococcus aureus, Escherichia coli, Pseudomonas aeruginosa, Enterococcus faecalis, Klebsiella pneumonia, Acinetobacter baumannii, Salmonella typhimarium, Listeria monocytogenes*, and *Streptococcus pyogenes*. The new strains of bacteria have been identified to exhibit antimicrobial activities against both Gram positive and Gram negative bacteria, and against 3 or more problematic bacterial strains.

Isolate G346a is a microorganism classified as a member of the genus by 16S rRNA sequencing. Its 16S rRNA sequence (SEQ ID NO: 1) as shown in FIG. 1 is 5.30% different from a closest match, *Paenibacillus illinoisensis*. It possesses an antimicrobial activity against a range of Gram positive and Gram negative bacteria.

Isolate 159 is a microorganism classified as a member of the genus *Enterococcus* based on 16S rRNA sequencing. Its 16S rRNA sequence (SEQ ID NO:2) as shown in FIG. 2 is 0.18% different from a closest match, *Enterococcus casseliflavus*. It possesses an antimicrobial activity against a range of Gram positive and Gram negative bacteria.

Functionally equivalent microorganisms of the antimicrobial microorganisms of the present invention are also provided. The term "a functionally equivalent microorganism" used herein refers to a microorganism that exhibits essentially the same characteristics and functions as an original microorganism. A functionally equivalent microorganism may be a mutant or variant derived from an original microorganism. The mutant or variant may be formed by various ways (e.g., by UV irradiation or by mutagenic chemicals). The term "essentially the same" used herein refers to being at least about 80%, 85%, 90%, 95%, 96%, 97%, 98%, or 99% identical.

A functionally equivalent microorganism of an antimicrobial microorganism is a microorganism that exhibits essentially the same antimicrobial activity, for example, having essentially the same inhibition effect on essentially the same microorganisms, as an original antimicrobial microorganism. A functionally equivalent microorganism may be a mutant or variant derived from an original antimicrobial microorganism. A functionally equivalent mutant or variant may comprise a nucleic acid sequence that is at least about 80%, 85%, 90%, 95%, 96%, 97%, 98%, or 99% identical to that of an original antimicrobial microorganism (e.g., SEQ ID NO: 1 of Isolate 346a, or SEQ ID NO: 2 of Isolate 159).

A biological, or liquid, culture of an antimicrobial microorganism of the present invention, or a functionally equivalent microorganism thereof, may be prepared by growing the microorganism, or the functionally equivalent microorganism, in a suitable culture medium. The techniques and suitable culture media for preparing a biological culture of a microorganism (e.g., a bacteria strain) are well known in the art.

According to another aspect of the present invention, an antimicrobial agent is provided. The term "an antimicrobial agent" used herein refers to an agent that exhibits an antimicrobial activity. The agent may be a chemical compound, a biological molecule (e.g., a nucleic acid, peptide or protein), or a combination thereof. The antimicrobial agent may be prepared by using an antimicrobial microorganism of the present invention, or a functionally equivalent microorganism thereof. For example, an antimicrobial agent may be prepared by purification and/or isolation from a biological culture, or a supernatant of the biological culture, of the microorganism, or a functionally equivalent microorganism thereof. The antimicrobial agent may comprise an amino acid sequence selected from the group consisting of SEQ ID NOs: 3-18. Also provided is a method for preparing an antimicrobial agent comprising using the antimicrobial microorganism of the present invention, or a functionally equivalent microorganism thereof.

According to a further aspect of the present invention, a method for treating a microbial infection in a subject in need thereof is provided. The method comprises administering to the subject an effective amount of the antimicrobial agent of the present invention. The subject is a mammal, for example, a mouse, rat, dog, pig or human, preferably a human. The effective amount will depend on the route of administration, the nature of the formulation, and the subject's condition. The antimicrobial agent may be formulated, for example, for an oral, sublingual, intranasal, intraocular, rectal, transdermal, mucosal, topical or parenteral administration.

The term "about" as used herein when referring to a measurable value such as an amount, a percentage, and the like, is meant to encompass variations of ±20% or ±10%, more preferably ±5%, even more preferably ±1%, and still more preferably ±0.1% from the specified value, as such variations are appropriate to perform the disclosed methods.

EXAMPLE 1

Antimicrobial Libraries

Microbial libraries of microorganisms containing previously unculturable species were established using quorum quenching technology, which disrupts the quorum sensing ability of bacteria. Each library consists of bacteria from several different natural sources, including: freshwater (pond), soil (corn field, grassy field), sewage, rumen fluid (cow), and compost pile (aerobic and anaerobic).

The libraries were screened for an antimicrobial activity. Microbial isolates of the libraries were screened for an antimicrobial activity using a Biological Growth Inhibition assay against the following indicator strains: *Acinetobacter baumannii, Enterococcus faecalis, Escherichia coli, Klebsiella-pneumoniae, Listeria monocytogenes, Pseudomonas aeruginosa, Salmonella typhimurium, Staphylococcus aureus*, and *Streptococcus pyogenes*. Library isolates were spotted on a lawn of the indicator organism. Plates were incubated for 24-48 hours and activity was observed as a zone of inhibition around the bacterial spot.

*E. coli* and *Bacillus* strains which contain antibiotic resistant plasmids were also screened against to discriminate lead antimicrobial agents, including compounds, from the following previously described antibiotics: ampicillin, kanamycin, streptomycin, spectinomycin, tetracycline, chloramphenicol, and erythromycin.

Novel bacteria were isolated in combination with the quorum-quenching enzyme Esterase, from porcine liver (Sigma E3019-20KU, 17 units/mg solid) as described in Example 1 in U.S. Pat. No. 7,494,810. According to 16S rRNA sequencing, approximately 50% of all characterized isolates were new species. As a result, novel bacteria were identified, after isolation, to contain an antimicrobial activity.

EXAMPLE 2

Antimicrobial Microorganisms

Approximately 100 isolates produced an antimicrobial activity against 3 or more problematic bacterial strains, both Gram positive and Gram negative, and were considered isolates of interest. Fifteen of these isolates, identified in TABLE 1, exhibited characteristics of special interest and were sent for 16S rRNA sequencing (by Accugenix, Newark Del., using conventional techniques) to determine their closest match with 16S rRNA sequences of known bacteria.

TABLE 1

| Isolate # | Closest Match, % Difference, Taxonomic Confidence Level | S.a. G+ | E. coli G- | Pseudo G- | K.p. G- | A.b. G- | E.f. G+ | Salmo G- | List. G+ | Strep. G+ |
|---|---|---|---|---|---|---|---|---|---|---|
| 6 | Serratia-proteamaculans-quinovora 1.23% Genus | 0.4 | 0.2 | | | | 0.25 | 0.1 | | |
| 17 | Pseudomonas-alcaligenes 1.15% Genus | 0.5 | 0.4 | | 0.15 | 0.35 | 0.2 | 0.2 | 0.25 | 0.2 |
| 138 | Paenibacillus-amylolyticus 6.03% No Match | 0.6 | | | 0.1 | 0.3 | | | 0.2 | 0.8 |
| 159 | Enterococcus-casseliflavus 0.28% Species | 1 | 0.4 | 0.3 | 0.05 | 0.1 | | 0.1 | | |
| 228 | Burkholderia-plantarii 2.00% Genus | | 0.3 | | 0.15 | 0.3 | | 0.4 | | |
| 375 | Pseudomonas-fulva 1.05% Genus | 0.4 | 0.3 | 0.1 | 0.15 | 0.3 | 0.1 | 0.2 | | 0.5 |
| 423 | Paenibacillus-amylolyticus 6.22% No Match | 0.6 | | | 0.1 | 0.3 | | | 0.3 | 0.7 |
| 457 | Pseudomonas-asplenii/putida 1.53% Genus | 0.2 | 0.3 | | 0.1 | 0.05 | 0.15 | 0.15 | | 0.3 |
| G266 | Pantoea-agglomerans 2.46% Genus | 0.7 | 1 | 0.1 | 0.05 | 0.5 | 0.7 | 0.3 | | 0.1 |
| G280 | Pantoea-ananatis 2.28% Genus | 1 | 1 | 0.1 | 0.05 | 0.4 | 0.6 | 0.2 | | 0.1 |
| G346a | Paenibacillus-illinoisensis 5.30% Genus | 0.6 | | | 0.15 | 0.3 | | | 0.25 | 0.7 |
| G505 | Enterobacter-asburiae 1.33% No Match | 0.3 | 0.3 | 0.05 | | | 0.3 | 0.4 | 0.25 | 0.3 |
| G507 | Enterobacter-asburiae 1.52% No Match | 0.3 | 0.3 | 0.05 | | | 0.3 | 0.4 | 0.25 | 0.3 |
| G522 | Enterobacter-asburiae 1.43% No Match | 0.3 | 0.3 | 0.05 | | | 0.3 | 0.4 | 0.25 | 0.3 |
| G524 | Enterobacter-asburiae 1.24% No Match | 0.3 | 0.3 | 0.05 | | | 0.3 | 0.4 | 0.25 | 0.3 |

TABLE 1 lists 15 novel isolates that demonstrate a broad range of antimicrobial activities against three or more of the problematic bacterial strains (both Gram positive and Gram negative) listed at the top of columns 3-11 in TABLE 1. TABLE 1 also lists, with reference to the novel isolates, their closest related species, and the level of antimicrobial activities of the various isolates. More specifically, for each isolate, TABLE 1 indicates its isolate number, Closest Match, Percentage Difference to the Closest Match, and taxonomic confidence level from sequencing, and antimicrobial activities against specific problematic bacterial strains measured in centimeters. This centimeter measurement is the Zone of Inhibition and measures the distance from the perimeter of the bacteria to the perimeter of the clear zone demonstrating an antimicrobial activity exhibited by each corresponding isolate.

Closest Match is the closest match of a related species to the sample when aligned in pairwise manner against the Sherlock Database.

The Percentage Difference to the Closest Match is the percent difference between the sample and the Closest Match. Mismatched basepairs, gaps, and ambiguity codes are all accounted for in this percentage.

Three Confidence Levels, representing the closeness of the novel isolate to the Closest Match, are identified in TABLE 1 as: (1) "Species," in which the difference between the novel isolate and the Closest Match is ≤1.00%) (2) "Genus," in which the difference is ≤5.00%) and (3) "No Match" with a Percentage Difference greater than 5%.

The following are the nine problematic bacterial strains abbreviated in TABLE 1 to which isolates exhibited resistance:

a. *Staphylococcus aureus* (Abbreviated S.a.)
b. *Escherichia coli* (Abbreviated *E. coli*)
c. *Pseudomonas aeruginosa* (Abbreviated Pseudo)
d. *Klebsiella pneumonia* (Abbreviated K.p.)
e. *Acinetobacter baumannii* (Abbreviated A.b.)
f. *Enterococcus faecalis* (Abbreviated E.f.)
g. *Salmonella typhimarium* (Abbreviated Salmo)
h. *Listeria monocytogenes* (Abbreviated List.)
i. *Streptococcus pyogenes* (Abbreviated Strep.)

Isolates G346a and 159 and their supernatants have been studied in more detail as described below.

EXAMPLE 3

Isolate G346a

Isolate G346a was analyzed to determine the Zone of Inhibition resulting from its antimicrobial activity, and to determine the activity of its supernatant, temperature stability and pH stability. The Zone of Inhibition was measured as the distance from the perimeter of the bacteria to the perimeter of the clear zone and recorded in centimeters.

a. Bacterial Screen

TABLE 2 illustrates the Zone of Inhibition of the G346a Isolate against the bacterial strains tested in Example 2.

TABLE 2

| Bacterial Strain | Zone of Inhibition (cm) |
| --- | --- |
| Staphylococcus aureus | 0.6 |
| Escherichia coli | 0.1 |
| Pseudomonas aeruginosa | neg |
| Klebsiella pneumonia | neg |
| Acinetobacter baumannii | 0.1 |
| Enterococcus faecalis | 0.4 |
| Salmonella typhimarium | neg |
| Listeria monocytogenes | 0.3 |
| Streptococcus pyogenes | 0.8 |

A "neg" result in the Bacterial ZOI (Zone of Inhibition) indicates no clear zone and no antimicrobial activity.

b. Supernatant

The antimicrobial activity of the supernatant of the G346a isolate was then determined. The isolate was grown in a biological, or liquid, culture, spun and filtered and then an antimicrobial screen was performed as follows:

1. Inoculate 20 µl bacterial suspension of G346a (OD600=0.5) into 20 mls Terrific Broth.
2. Incubate at 32° C., shaking at 200 rpm for 24 hours.
3. Centrifuge bacterial culture at 10,000 rpm for 30 mins.
4. Sterilize supernatant using 0.4 µ filter apparatus.

TABLE 3

| Bacterial Strain | Bacterial ZOI (cm) | Supernatant Activity |
| --- | --- | --- |
| S.a. | 0.6 | pos |
| E. coli | 0.1 | neg |
| P.a. | neg | neg |
| K.p. | neg | neg |
| A.b. | 0.1 | neg |
| E.f. | 0.4 | pos |
| Salmo | neg | neg |
| List. | 0.3 | pos |
| Strep | 0.8 | pos |

TABLE 3 sets forth the Bacterial Zone of Inhibition and Supernatant Activity of the G346a Supernatant. A "neg" result in the Bacterial ZOI (Zone of Inhibition) indicates no clear zone and no antimicrobial activity.

c. Temperature Stability

The Temperature Stability of the G346a supernatant was tested against a control. The G346a supernatant was incubated at different temperatures for 24-72 hours to observe stability. The G346a supernatant was plated on a S.a. bacterial strain plate and the plate incubated overnight. The results are shown in TABLE 4. A "pos" indicates a positive result where the G346a supernatant exhibited antimicrobial activity at the corresponding temperature and time. A "neg" indicates a negative result where the G346a supernatant exhibited no antimicrobial activity at the corresponding temperature and time.

TABLE 4

| Temperature | 24 hrs | 48 hrs | 72 hrs |
| --- | --- | --- | --- |
| 4° C. | pos | pos | pos |
| 28° C. | pos | pos | pos |
| 37° C. | pos | neg | neg |
| 50° C. | partial | neg | neg |
| 70° C. | neg | neg | neg |
| Control | pos | pos | pos | d. pH Stability

The pH stability of the G346a supernatant was tested. The pH of G346a supernatant was adjusted to pH 3 and pH 10 using 1 M HCl and 1M NaOH. The G346a supernatant was incubated at 37° C. for 2 hours and neutralized to the original pH (7.3) before screening. 20 µl of the G346a supernatant was plated on a S.a. bacterial strain plate to observe the effect of pH on the supernatant. The results indicated that the G346a supernatant retains full activity at pH 3 (acidic conditions) but does not retain full activity at pH 10 (basic conditions).

e. Antimicrobial Activity against Staphylococcus aureus

Liquid cultures of Staphylococcus aureus were grown for eight hours and the optical density of the cultures was taken every hour. After four hours, at the exponential growth phase, G346a supernatant was added to two samples of the Staphylococcus aureus culture. The experiment was carried out in duplicate. FIG. 3 illustrates the average bacteriolytic effect when the G346a supernatant was added during the exponential growth phase compared to two control samples to which G346a was not added.

f. Antimicrobial Activity against Acinetobacter baumannii

Figure 4:
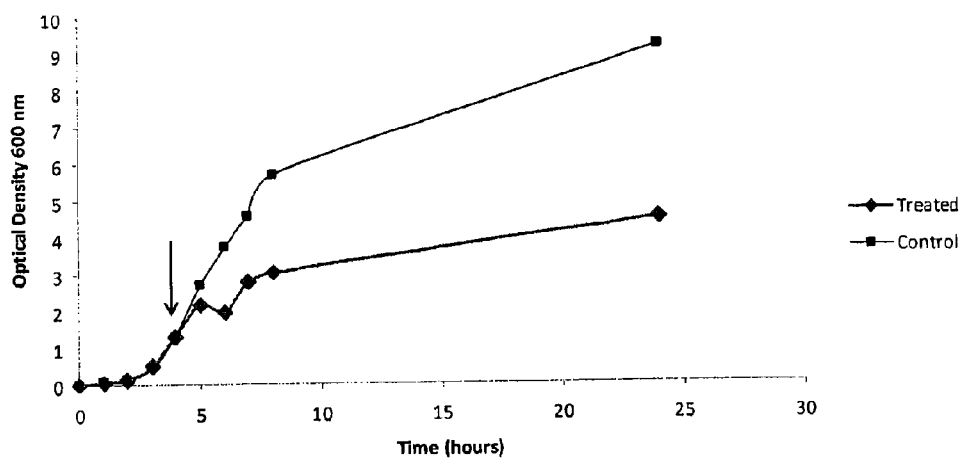
FIG. 4 illustrates the antimicrobial activity of Isolate G346a (ATCC accession number PTA-11858) against *Acinetobacter baumannii* (*A. baumannii*).

Liquid cultures of Acinetobacter baumannii were grown for twenty-four hours and the optical density of the cultures was taken every hour for eight hours and again after twenty-four hours of growth. After four hours, at the exponential growth phase, G346a concentrated supernatant was added to two samples of the Acinetobacter baumannii culture. The experiment was carried out in duplicate. FIG. 4 illustrates the bacteriostatic effect when the G346a concentrated supernatant was added during the exponential growth phase compared to two control samples to which G346a was not added.

g. Antimicrobial Agent

A concentrated antimicrobial compound (CAC) was prepared as an antimicrobial agent. 2.1 L of an overnight bacterial culture of G346a was centrifuged at 10,000× g for 20 min, and then subject to 0.2 µm filtration. The supernatant was subject to 10-15% TCA precipitation for 1 hour, and then centrifugation at 4,000× for 20 min. The pellet was re-suspended in 3 mL 50 mM $NH_4HCO_3$, and then neutralized with 320 µL $NH_4OH$. The resulting concentrated antimicrobial compound (CAC) was tested for its antimicrobial activity against susceptible and resistant strains as shown in TABLE 5.

TABLE 5

| Compound | S. aureus | S. aureus (MRSA) | A. baumannii | A. Baumannii (MDR) |
| --- | --- | --- | --- | --- |
| G346a sup. | 1:20 | N/A | No inhibition | N/A |
| G346a CAC | 1:1,280 | 1:1,280 | 1:80 | 1:320 |
| Ampicillin (1.28 mg/ml) | 1:5,120 | No Inhibition | 1:20 | No Inhibition |
| Carbenicillin (1.28 mg/ml) | 1:320 | No Inhibition | 1:20 | No Inhibition |

TABLE 5-continued

| Compound | S. aureus | S. aureus (MRSA) | A. baumannii | A. Baumannii (MDR) |
|---|---|---|---|---|
| Doxycycline (1.28 mg/ml) | 1:5,120 | 1:5,120 | 1:5,120 | 1:640 |

The antimicrobial agent may further be purified and/or isolated from the concentrated antimicrobial compound (CAC) of G346a using techniques conventionally known in the art. The components of the antimicrobial agent may be determined using suitable analysis (e.g., mass spectrometry analysis). For example, the CAC of G346a was purified using a 5-ml HiTrap™ hydrophobic interaction chromatography (HIC) column prepacked with Phenyl Sepharose™ High Performance (HP). Active fractions were lyophilized, and further purified using a C18 Reverse-Phase (RP) HPLC column. A single peak of interest was observed, and subject to mass spectrometry analysis. The LC/MS results indicate two potential peptide components in the peak with molecular masses of 3348.2 Da and 5961.9 Da. These two components were further analyzed using MS/MS techniques, and found to contain one of the following amino acid sequences:

| Sequence | SEQ ID NO |
|---|---|
| KFIKSI | 3 |
| KFIKSL | 4 |
| KFIQSI | 5 |
| KFIQSL | 6 |
| KFLKSI | 7 |
| KFLKSL | 8 |
| KFLQSI | 9 |
| KFLQSL | 10 |
| QFIKSI | 11 |
| QFIKSL | 12 |
| QFIQSI | 13 |
| QFIQSL | 14 |
| QFLKSI | 15 |
| QFLKSL | 16 |
| QFLQSI | 17 |
| QFLQSL | 18 |

EXAMPLE 4.

Isolate 159

Isolate 159 was also tested to determine the Zone of Inhibition resulting from its antimicrobial activity, and to determine its supernatant activity, temperature stability and pH stability.

a. Bacterial Screen

TABLE 6 illustrates the Zone of Inhibition of Isolate 159 against the bacterial strains tested in Example 2.

TABLE 6

| Bacterial strain | Zone of Inhibition (cm) |
|---|---|
| Staphylococcus aureus | 1 |
| Escherichia coli | 0.4 |
| Pseudomonas aeruginosa | 0.3 |
| Klebsiella pneumonia | 0.05 |
| Acinetobacter baumannii | 0.1 |
| Enterococcus faecalis | neg |
| Salmonella typhimurium | 0.1 |
| Listeria monocytogenes | neg |
| Streptococcus pyogenes | neg |

A "neg" result in the Bacterial ZOI (Zone of Inhibition) indicates no clear zone and no antimicrobial activity.

b. Supernatant

The antimicrobial activity of the supernatant of isolate 159 was then determined.

The isolate was obtained via a Cross-Species induction method active against *Pseudomonas aeruginosa* (P.a.) in order to induce production of the antimicrobial, after which the 159/P.a. isolate was grown in liquid culture, spun and filtered and used for an antimicrobial screen. The process was conducted as follows:

1. a. Inoculate 20 μl bacterial suspension of 159 (OD600 =0.5) into 20 mls Terrific Broth.
   b. Separately, inoculate 20 μl bacterial suspension of *Pseudomonas aeruginosa* (OD600=0.5) into 20 mls Terrific Broth.
2. Incubate both cultures at 32° C., shaking at 200 rpm for 8 hours.
3. Add 200 μl *Pseudomonas aeruginosa* culture to 159 culture.
4. Incubate mixed culture for total period of 24 hours.
5. Centrifuge bacterial culture at 10,000 rpm for 30 mins.
6. Sterilize supernatant using 0.4 μ filter apparatus.

A positive result was exhibited for supernatant activity in the presence of *Pseudomonas aeruginosa*.

c. Temperature Stability

The Temperature Stability of the 159/P.a. supernatant was tested against a control. The 159/P.a. supernatant was incubated at different temperatures for 24-72 hours to observe stability. The 159/P.a. supernatant was plated on P.a. bacterial strain plate and the plate incubated overnight. The results are shown in TABLE 6. A "pos" indicates a positive result where the 159/P.a. supernatant exhibited an antimicrobial activity at the corresponding temperature and time. A "neg" indicates a negative result where the 159/P.a. supernatant exhibited no antimicrobial activity at the corresponding temperature and time.

TABLE 7

| Temperature | 24 hrs | 48 hrs | 72 hrs |
|---|---|---|---|
| 4° C. | pos | pos | pos |
| 28° C. | pos | pos | pos |
| 37° C. | pos | neg | neg |
| 50° C. | partial | neg | neg |
| 70° C. | neg | neg | neg |
| Control | pos | pos | pos | d. pH Stability

The pH stability of the 159/P.a. supernatant was tested. The pH of 159/P.a. supernatant was adjusted to pH 3 and pH 10 using 1 M HCl and 1M NaOH. The 159/P.a. supernatant was incubated at 37° C. for 2 hours and neutralized to the original pH (7-7.8) before screening. 20 μl of the 159/P.a. supernatant was plated on P.a. bacterial strain plate to observe the effect of pH on the supernatant. The results indicated that the 159/P.a. supernatant is not effected by basic conditions.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

What is claimed:

1. A method for treating a microbial infection in a subject in need thereof, comprising administering to the subject an effective amount of an antimicrobial agent, wherein the antimicrobial agent is prepared by a method comprising
   (a) growing a microorganism having an ATCC Patent Deposit Designation of PTA-11858 in a culture medium, and
   (b) purifying or isolating the antimicrobial agent from the culture medium of step (a).

2. The method of claim 1, wherein the subject is a mammal selected from the group consisting of a mouse, rat, dog, pig and human.

3. The method of claim 2, wherein the subject is a human.

4. The method of claim 1, wherein the antimicrobial agent is formulated for oral, sublingual, intranasal, intraocular, rectal, transdermal, mucosal, topical or parenteral administration.

* * * * *

SEQUENCE LISTING

<160> NUMBER OF SEQ ID NOS: 18

<210> SEQ ID NO 1
<211> LENGTH: 1548
<212> TYPE: DNA
<213> ORGANISM: Paenibacillus

<400> SEQUENCE: 1

| | | | | | |
|---|---|---|---|---|---|
| tggagagttt | gatcctggct | caggacgaac | gctggcggcg | tgcctaatac | atgcaagtcg | 60 |
| agcggagaat | raargaagct | tgcttctttc | attcttagcg | gcggacgggt | gagtaacacg | 120 |
| taggcaacct | gccctcaagc | ttgggacaac | taccggaaac | ggtagctaat | accgaataca | 180 |
| tgatttgttc | gcctgaacga | atytggaaag | acggagcaat | ctgtcacttg | aggatgggcc | 240 |
| tgcggcgcat | tagctagttg | gtgaggtaac | ggctcaccaa | ggcgacgatg | cgtagccgac | 300 |
| ctgagagggt | gatcggccac | actgggactg | agacacggcc | cagactccta | cgggaggcag | 360 |
| cagtagggaa | tcttccgcaa | tggacgcaag | tctgacggag | caacgccgcg | tgagtgatga | 420 |
| aggttttcgg | atcgtaaagc | tctgttgcca | gggaagaacg | tcygrgttag | taactgaact | 480 |
| crgagtgacg | gtacctgaga | agaaagcccc | ggctaactac | gtgccagcag | ccgcggtaat | 540 |
| acgtagggg | caagcgttgt | ccggaattat | tgggcgtaaa | gcgcgcgcag | gcggcttttt | 600 |
| aagtccggtg | tcacagccca | aggctcaacc | ttgggtcgca | ctggaaactg | gagagcttga | 660 |
| gtacagaaga | ggaaagtgga | attccacgtg | tagcggtgaa | atgcgtagag | atgtggagga | 720 |
| acaccagtgg | cgaaggcgac | tttctgggct | gtaactgacg | ctgaggcgcg | aaagcgtggg | 780 |
| gagcaaacag | gattagatac | cctggtagtc | cacgccgtaa | acgatgaatg | ctaggtgtta | 840 |
| ggggtttcga | taccctggt | gccgaagtta | acacattaag | cattccgcct | ggggagtacg | 900 |
| gtcgcaagac | tgaaactcaa | aggaattgac | ggggacccgc | acaagcagtg | gagtatgtgg | 960 |
| tttaattcga | agcaacgcga | agaaccttac | caagtcttga | catcccttg | accggactag | 1020 |
| agatagtcct | ttccttcggg | acaaaggaga | caggtggtgc | atggttgtcg | tcagctcgtg | 1080 |
| tcgtgagatg | ttgggttaag | tcccgcaacg | agcgcaaccc | ttatgcttag | ttgccagcac | 1140 |
| atcatggtgg | gcactctaag | cagactgccg | gtgacaaacc | ggaggaaggt | ggggatgacg | 1200 |
| tcaaatcatc | atgccccta | tgacttgggc | tacacacgta | ctacaatggc | cggtacaacg | 1260 |
| ggaagcaata | tcgcaagatg | gagccaatcc | ttaaaagccg | gtctcagttc | ggattgcagg | 1320 |
| ctgcaactcg | cctgcatgaa | gtcggaattg | ctagtaatcg | cggatcagca | tgccgcggtg | 1380 |
| aatacgttcc | cgggtcttgt | acacaccgcc | cgtcacacca | cgagagtttg | caacacccga | 1440 |
| agtcggtggg | gtaaccgcaa | ggagccagcc | gccgaaggtg | gggtagatga | ttggggtgaa | 1500 |
| gtcgtaacaa | ggtagccgta | tcggaaggtg | cggytggatc | acctcctt | | 1548 |

<210> SEQ ID NO 2
<211> LENGTH: 1555
<212> TYPE: DNA
<213> ORGANISM: Enterococcus casseliflavus

<400> SEQUENCE: 2

| | | | | | |
|---|---|---|---|---|---|
| tggagagttt | gatcctggct | caggacgaac | gctggcggcg | tgcctaatac | atgcaagtcg | 60 |
| aacgcttttt | ctttcaccgg | agcttgctcc | aycgaaagaa | aaagagtggc | gaacgggtga | 120 |
| gtaacacgtg | ggtaacctgc | ccatcagaag | gggataacac | ttggaaacag | gtgctaatac | 180 |
| cgtataacac | tatttccgc | atggaagaaa | gttgaaaggc | gcttttgcgt | cactgatgga | 240 |
| tggacccgcg | gtgcattagc | tagttggtga | ggtaacggct | caccaaggca | acgatgcata | 300 |

```
gccgacctga gagggtgatc ggccacactg ggactgagac acggcccaga ctcctacggg    360
aggcagcagt agggaatctt cggcaatgga cgaaagtctg accgagcaac gccgcgtgag    420
tgaagaaggt tttcggatcg taaaactctg ttgttagaga agaacaagga tgagagtaaa    480
acgttcatcc cttgacggta tctaaccaga aagccacggc taactacgtg ccagcagccg    540
cggtaatacg taggtggcaa gcgttgtccg gatttattgg gcgtaaagcg agcgcaggcg    600
gtttcttaag tctgatgtga aagccccggg ctcaaccggg gagggtcatt ggaaactggg    660
agacttgagt gcagaagagg agagtggaat tccatgtgta gcggtgaaat gcgtagatat    720
atggaggaac accagtggcg aaggcggctc tctggtctgt aactgacgct gaggctcgaa    780
agcgtgggga gcgaacagga ttagataccc tggtagtcca cgccgtaaac gatgagtgct    840
aagtgttgga gggtttccgc ccttcagtgc tgcagcaaac gcattaagca ctccgcctgg    900
ggagtacgac cgcaaggttg aaactcaaag gaattgacgg gggcccgcac aagcggtgga    960
gcatgtggtt taattcgaag caacgcgaag aaccttacca ggtcttgaca tcctttgacc   1020
actctagaga tagagcttcc ccttcggggg caaagtgaca ggtggtgcat ggttgtcgtc   1080
agctcgtgtc gtgagatgtt gggttaagtc ccgcaacgag cgcaacccct attgttagtt   1140
gccatcattt agttgggcac tctagcgaga ctgccggtga caaaccggag gaaggtgggg   1200
atgacgtcaa atcatcatgc cccttatgac ctgggctaca cacgtgctac aatgggaagt   1260
acaacgagtt gcgaagtcgc gaggctaagc taatctctta aagcttctct cagttcggat   1320
tgtaggctgc aactcgccta catgaagccg gaatcgctag taatcgcgga tcagcacgcc   1380
gcggtgaata cgttcccggg ccttgtacac accgcccgtc acaccacgag agtttgtaac   1440
acccgaagtc ggtgaggtaa ccttttggga gccagccgcc taaggtggga tagatgattg   1500
gggtgaagtc gtaacaaggt agccgtatcg gaaggtgcgg ctggatcacc tcctt        1555
```

<210> SEQ ID NO 3
<211> LENGTH: 6
<212> TYPE: PRT
<213> ORGANISM: Paenibacillus

<400> SEQUENCE: 3

Lys Phe Ile Lys Ser Ile
1               5

<210> SEQ ID NO 4
<211> LENGTH: 6
<212> TYPE: PRT
<213> ORGANISM: Paenibacillus

<400> SEQUENCE: 4

Lys Phe Ile Lys Ser Leu
1               5

<210> SEQ ID NO 5
<211> LENGTH: 6
<212> TYPE: PRT
<213> ORGANISM: Paenibacillus

<400> SEQUENCE: 5

Lys Phe Ile Gln Ser Ile
1               5

<210> SEQ ID NO 6
<211> LENGTH: 6

```
<212> TYPE: PRT
<213> ORGANISM: Paenibacillus

<400> SEQUENCE: 6

Lys Phe Ile Gln Ser Leu
1               5

<210> SEQ ID NO 7
<211> LENGTH: 6
<212> TYPE: PRT
<213> ORGANISM: Paenibacillus

<400> SEQUENCE: 7

Lys Phe Leu Lys Ser Ile
1               5

<210> SEQ ID NO 8
<211> LENGTH: 6
<212> TYPE: PRT
<213> ORGANISM: Paenibacillus

<400> SEQUENCE: 8

Lys Phe Leu Lys Ser Leu
1               5

<210> SEQ ID NO 9
<211> LENGTH: 6
<212> TYPE: PRT
<213> ORGANISM: Paenibacillus

<400> SEQUENCE: 9

Lys Phe Leu Gln Ser Ile
1               5

<210> SEQ ID NO 10
<211> LENGTH: 6
<212> TYPE: PRT
<213> ORGANISM: Paenibacillus

<400> SEQUENCE: 10

Lys Phe Leu Gln Ser Leu
1               5

<210> SEQ ID NO 11
<211> LENGTH: 6
<212> TYPE: PRT
<213> ORGANISM: Paenibacillus

<400> SEQUENCE: 11

Gln Phe Ile Lys Ser Ile
1               5

<210> SEQ ID NO 12
<211> LENGTH: 6
<212> TYPE: PRT
<213> ORGANISM: Paenibacillus

<400> SEQUENCE: 12

Gln Phe Ile Lys Ser Leu
1               5

<210> SEQ ID NO 13
<211> LENGTH: 6
<212> TYPE: PRT
<213> ORGANISM: Paenibacillus
```

```
<400> SEQUENCE: 13

Gln Phe Ile Gln Ser Ile
1               5

<210> SEQ ID NO 14
<211> LENGTH: 6
<212> TYPE: PRT
<213> ORGANISM: Paenibacillus

<400> SEQUENCE: 14

Gln Phe Ile Gln Ser Leu
1               5

<210> SEQ ID NO 15
<211> LENGTH: 6
<212> TYPE: PRT
<213> ORGANISM: Paenibacillus

<400> SEQUENCE: 15

Gln Phe Leu Lys Ser Ile
1               5

<210> SEQ ID NO 16
<211> LENGTH: 6
<212> TYPE: PRT
<213> ORGANISM: Paenibacillus

<400> SEQUENCE: 16

Gln Phe Leu Lys Ser Leu
1               5

<210> SEQ ID NO 17
<211> LENGTH: 6
<212> TYPE: PRT
<213> ORGANISM: Paenibacillus

<400> SEQUENCE: 17

Gln Phe Leu Gln Ser Ile
1               5

<210> SEQ ID NO 18
<211> LENGTH: 6
<212> TYPE: PRT
<213> ORGANISM: Paenibacillus

<400> SEQUENCE: 18

Gln Phe Leu Gln Ser Leu
1               5
```